US00PP12924P2

(12) United States Plant Patent
Bergman

(10) Patent No.: US PP12,924 P2
(45) Date of Patent: Sep. 3, 2002

(54) CHRYSANTHEMUM PLANT NAMED 'YELLOW YODANVILLE'

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/774,359

(22) Filed: Feb. 1, 2001

(51) Int. Cl.[7] ..... A01H 5/00

(52) U.S. Cl. ..... Plt./289

(58) Field of Search ..... Plt./289

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Chrysanthemum plant named 'Yellow Yodanville', characterized by its uniform and upright plant habit; strong, moderately vigorous, and freely branching growth habit; dark green foliage; uniform flowering response; early flowering, eight-week response time; large decorative-type inflorescences that are about 9.6 cm in diameter; bright yellow ray florets that twist slightly as inflorescences develop; and excellent postproduction longevity with plants maintaining good substance and color for at least four weeks in an interior environment.

1 Drawing Sheet

BACKGROUND OF THE INVENTION

The present Invention relates to a new and distinct cultivar of Chrysanthemum plant, botanically known as *Chrysanthemum×morifolium* and herinafter referred to by the name 'Yellow Yodanville'.

The new Chrysanthemum is a product of a mutation induction program conducted by the Inventor in Fort Myers, Fla. The objective of the program is to create new potted Chrysanthemum cultivars that are suitable for year-round production with uniform plant growth habit, good vigor, desirable inflorescence form and floret colors, fast response time, and excellent prostproduction longevity.

The new Chrysanthemum originated by exposing unrooted cuttings of a proprietary Chrysanthemum seedling selection identified as YB-5273, not patented, to X-ray radiation in October, 1997 in Fort Myers, Fla. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Fort Myers, Fla. The new Chrysanthemum was discovered and selected by the Inventor as a single flowering plant within this population in April, 1998, in Fort Myers, Fla. The selection of this plant was based on its uniform plant growth habit, good vigor, desirable inflorescence form and floret colors, fast response time, and excellent postproduction longevity. Plants of the new Chrysanthemum differ primarily from plants of the parent selection and the cultivars Yodanville (disclosed in U.S. Plant Patent application Ser. No. 09/774,370), Dark Yodanville (disclosed in U.S. Plant Patent application Ser. No. 09/774,357), and Orange Yodanville (disclosed in U.S. Plant Patent application Ser. No. 09/774,358) in ray floret color.

Asexual reproduction of the new Chrysanthemum by vegetative tip cuttings was first conducted in Fort Myers, Fla. in July, 1998. Asexual reproduction by cuttings has shown that the unique features of this new Chrysanthemum are stable and reproduced true to type in successive generations.

SUMMARY OF THE INVENTION

The cultivar Yellow Yodanville has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yellow Yodanville'. These characteristics in combination distinguish 'Yellow Yodanville' as a new and distinct Chrysanthemum:

1. Uniform and upright plant habit.
2. Strong, moderately vigorous, and freely branching growth habit.
3. Dark green foliage.
4. Uniform flowering response.
5. Typically grown as a disbud-type.
6. Early flowering, eight-week response time.
7. Large decorative-type inflorescences that are about 9.6 cm in diameter.
8. Bright yellow ray florets that twist slightly as the inflorescences develop giving inflorescences a cactus-dahlia appearance.
9. Excellent postproduction longevity with plants maintaining good substance and color for at least four weeks in an interior environment.

Plants of the new Chrysanthemum can be compared to plants of the cultivar Kory, disclosed in U.S. Plant Pat. No. 6,949. In side-by-side comparisons conducted by the Inventor in Salinas, Calif., plants of the new Chrysanthemum differ from plants of the cultivar Kory in the following characteristics:

1. Plants of the new Chrysanthemum are more outwardly spreading and more vigorous than plants of the cultivar Kory.

2. Plants of the new Chrysanthemum have larger inflorescences than plants of the cultivar Kory.

3. Ray florets of the new Chrysanthemum twist slightly with development whereas ray florets of the cultivar Kory do not twist with development.

4. Inflorescences of the new Chrysanthemum produce fewer disc florets than inflorescences of the cultivar Kory.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph at the top of the sheet comprises a top perspective view of a typical flowering plant of 'Yellow Yodanville' grown a disbud-type.

The photograph at the bottom of the sheet comprises a close-up view of typical inflorescences of 'Yellow Yodanville' grown as a disbud-type.

DETAILED BOTANICAL DESCRIPTION

In the following description, color references are made to The Royal Horticultural Society Colour Chart except where general terms of ordinary dictionary significance are used. The following observations and measurements describe plants grown and flowered during the autumn in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 4,000 to 6,000 foot-candles. Four unrooted cuttings were directly stuck in 15-cm containers, exposed to long day/short night conditions, and pinched once about 14 days later. At that time, the photoinductive short day/long night treatments were started. Plants used for this description were grown as disbud-types. Measurements and numerical values represent averages of typical flowering plants.

Botanical classification: *Chrysanthemum×morifolium* cultivar Yellow Yodanville.

Commercial classification: Decorative-type potted Chrysanthemum.

Parentage: Induced mutation of a proprietary *Chrysanthemum×morifolium* seedling selection identified as code number YB-5273, not patented.

Propagation:

*Type*.—Terminal tip cuttings.

*Time to initiate roots*.—About four days at 21° C.

*Time to produce a rooted cutting*.—About ten days at 21° C.

*Root description*.—Fibrous and well-branched.

Plant description:

*Appearance*.—Herbaceous decorative-type potted Chrysanthemum typically grown as a disbud-type. Stems upright and outwardly spreading giving a uniformly mounded appearance to the plant. Freely branching, about four lateral branches develop after removal of terminal apex (pinching); dense and full plants. Moderate vigor.

*Plant height*.—About 26 cm.

*Plant width*.—About 43 cm.

*Lateral branches*.—Length: About 23 cm. Diameter: About 4.5 mm. Internode length: About 1.4 cm. Strength: Very strong. Texture: Pubescent. Color: 144A to 146A.

*Foliage description*.—Arrangement: Alternate. Quanitity of leaves per lateral stem: About 15. Length: About 8.3 cm. Width: About 7.1 cm. Apex: Cuspidate. Base: Mostly truncate. Margin: Palmately lobed, sinuses between lateral lobes mostly convergent. Texture: Upper and lower surfaces with very fine pubescence; veins prominent on lower surface. Color: Young foliage, upper surface: Darker than 147A; glossy. Young foliage, lower surface: Darker than 147B. Mature foliage, upper surface: Darker than 147A; glossy. Mature foliage, lower surface: Darker than 147B. Venation, upper surface: 147A. Venation, lower surface: 147B. Petiole length: About 1.7 cm. Petiole diameter: About 3 mm. Petiole color: 147B to 147C.

Inflorescence description:

*Appearance*.—Decorative-type inflorescence form with elongated oblong-shaped ray florets. Inflorescences borne on terminals above foliage. Disk and ray florets arranged acropetally on a capitulum. Not fragrant. Typically grown as a disbud-type.

*Flowering response*.—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about eight weeks later.

*Postproduction longevity*.—Inflorescences maintain good color and substance for at least four weeks in an interior environment.

*Quantity of inflorescences*.—Produced as a disbud-type, all the lateral inflorescences are removed leaving only the terminal inflorescence.

*Inflorescence bud*.—Height: About 5 mm. Diameter: About 8 mm. Color: Close to 143A.

*Inflorescence size*.—Diameter: Large, about 9.6 cm. Depth (height): About 2.8 cm. Diameter of disc: About 7.5 mm, inconspicious. Receptacle diameter: About 1.1 cm.

*Ray florets*.—Shape: Elongated-oblong. Orientation: Initially upright, then about 90° from vertical or perpendicular to the peduncle. Aspect: Initially incurved to flat to somewhat convex and slightly twisted. Length: About 4.9 cm. Width: About 1.1 cm. Corolla tube length: About 3 mm. Apex: Emarginate. Base: Attenuate; short corolla tube. Margin: Entire. Texture: Smooth, glabrous, satiny. Number of ray florets per inflorescence: Numerous, about 288. Color: When opening, upper surface: Initially, 145A, then 7B to 7A. When opening, lower surface: 7D. Fully opened, upper surface: 7A. Fully opened, lower surface: 7D.

*Disc florets*.—Arrangement: Massed at center of receptacle, inconspicuous. Shape: Tubular, elongated. Apex: Five-pointed. Length: About 5.5 mm. Width: Apex, about 1.5 mm; base, about 1 mm. Number of disc florets per inflorescence: About 51. Color: Immature: 144A to 154A. Mature: Apex: 9A. Mid-section and base: Close to 155D.

*Reproductive organs*.—Androecium: Present on disc florets only. Anther color: 9A. Pollen amount: None. Gynoecium: Present on both ray and disc florets. Pistil color: Greenish white.

*Seed*.—Seed production has not been observed.

Disease resistance: Resistance to pathogens common to Chrysanthemums has not been observed on plants grown under commercial greenhouse conditions.

It is claimed:

1. A new and distinct cultivar of Chrysanthemum plant named 'Yellow Yodanville', as illustrated and described.

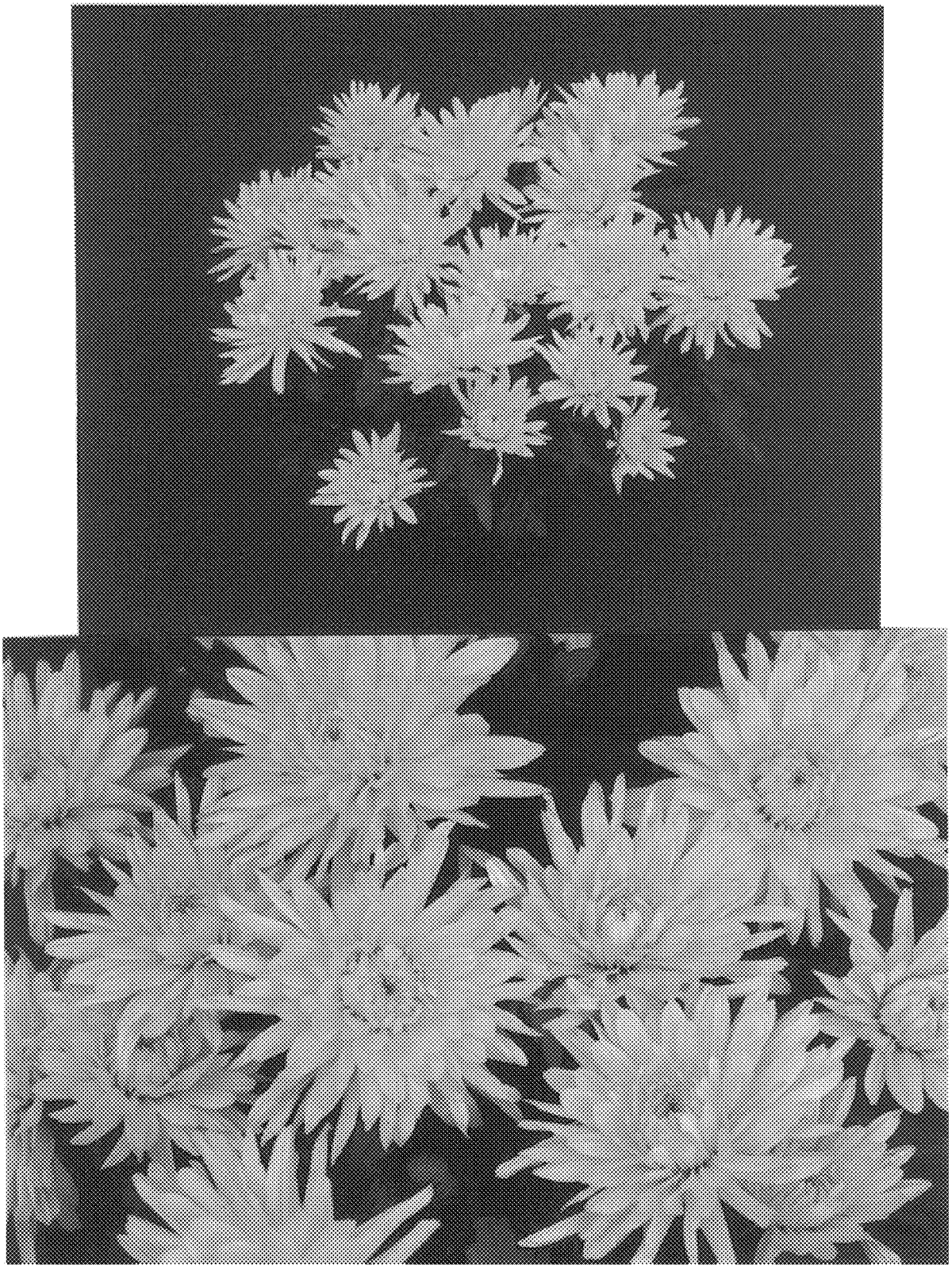

* * * * *